United States Patent [19]

Berg

[11] Patent Number: 5,382,329

[45] Date of Patent: Jan. 17, 1995

[54] SEPARATION OF 1-DECENE FROM DECANE BY AZEOTROPIC DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 208,695

[22] Filed: Mar. 11, 1994

[51] Int. Cl.6 .......................... B01D 3/36; C07C 7/06
[52] U.S. Cl. ........................................ 203/60; 203/63; 585/866
[58] Field of Search ............................ 203/60, 63, 56; 585/866

[56] References Cited

U.S. PATENT DOCUMENTS

| 2,461,993 | 2/1949 | McKinnis | 203/62 |
| 5,085,740 | 2/1992 | Lee et al. | 203/58 |
| 5,100,515 | 3/1992 | Lee et al. | 203/56 |

*Primary Examiner*—Wilbur Bascomb, Jr.

[57] ABSTRACT

1-Decene is difficult to separate from decane by conventional distillation or rectification because of the proximity of their boiling points. 1-Decene can be readily separated from decane by azeotropic distillation. Effective agents are methyl propionate, ethyl butyrate and methyl t-butyl ether.

1 Claim, No Drawings

SEPARATION OF 1-DECENE FROM DECANE BY AZEOTROPIC DISTILLATION

FIELD OF THE INVENTION

This invention relates to a method for separating 1-decene from n-decane using certain organic liquids as the agent in azeotropic distillation.

DESCRIPTION OF PRIOR ART

Azeotropic distillation is the method of separating close boiling compounds or azeotropes from each other by carrying out the distillation in a multiplate rectification column in the presence of an added liquid said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

In the Fischer-Tropsch process for converting carbon monoxide and hydrogen into liquids, gases and waxes, hundreds of different hydrocarbons and oxygenated compounds are formed, most of them in very small amounts. One valuable compound occurring in reasonable quantities is 1-decene, b.p.=173.5° C. When this compound is separated by precision fractionation, all but the closest boiling compounds are separated. They are decane, b.p.=174° C. and 2-octanone, b.p.=173° C. Azeotropic distillation would be an attractive method of effecting the separation of 1-decene from decane and 2-octanone if agents can be found that (1) will create a large apparent relative volatility between 1-decene decane and (2) are easy to recover from 1-decene. 1-Decene and decane boil less than less than a degree apart and thus are impractical to separate by conventional rectification. Table 1 shows the relative volatility required to get 99% purity. With no agent, the relative volatility is 1.11 and 117 actual plates are required. With an agent giving a relative volatility of 1.6, twenty-seven plates are required.

TABLE 1

Theoretical and Actual Plates Required vs. Relative Volatility for 1-Decene - Decane Separation

| Relative Volatility | Theoretical Plates Required At Total Reflux, 99% Purity | Actual Plates Required, 75% Efficiency |
| --- | --- | --- |
| 1.11 | 88 | 117 |
| 1.3 | 35 | 47 |
| 1.6 | 20 | 27 |

OBJECTIVE OF THE INVENTION

The object of this invention is to provide a process or method of azeotropic distillation that will enhance the relative volatility of 1-decene from decane in their separation in a rectification column. It is a further object of this invention to identify organic compound which in addition to the above constraints, are stable, can be separated from 1-decane and recycled to the azeotrope column with little decomposition.

SUMMARY OF THE INVENTION

The objects of this invention are provided by a process for separating 1-decene from decane which entails the use of certain organic compounds as the agent in azeotropic distillation.

DETAILED DESCRIPTION OF THE INVENTION

I have discovered that certain organic compounds will greatly improve the relative volatility of 1-decene to decane and permit the separation of 1-decene from decane by rectification when employed as the agent in extractive distillation. They are methyl acetate, methyl formate, methyl propionate, ethyl butyrate, methyl t-butyl ether, t-amyl methyl ether and isopropyl ether.

TABLE 2

Effective Azeotropic Distillation Agents For Separating 1-Decene from Decane

| Compounds | Relative Volatility |
| --- | --- |
| Methyl acetate | 1.2 |
| Methyl formate | 1.3 |
| Methyl propionate | 1.5 |
| Ethyl butyrate | 1.65 |
| Methyl t-butyl ether | 1.45 |
| t-Amyl methyl ether | 1.25 |
| Isopropyl ether | 1.5 |

THE USEFULNESS OF THE INVENTION

The usefulness or utility of this invention can be demonstrated by referring to the data presented in Tables 1 and 2. All of the successful agents show that 1-decene can be separated from decane by means of azeotropic distillation in a rectification column and that the ease of separation as measured by relative volatility is considerable.

WORKING EXAMPLES

Example 1

Twenty grams of decane, 80 grams of 1-decane and 50 grams of methyl propionate were charged to a vapor-liquid equilibrium still and refluxed for five hours. Analysis indicated a vapor composition of 15.5% decane, 84.5% 1-decene; a liquid composition of 21.4% decane, 78.6% 1-decene. This is a relative volatility of 1.48.

Example 2

One hundred grams of 1-decene, 30 grams of decane and 150 grams of ethyl butyrate were placed in the stillpot of an 5.6 theoretical plate glass perforated plate rectification column and refluxed for three hours. The overhead composition was 1.6% decane, 98.4% 1-decene; the bottoms composition was 20.5% decane, 79.5% 1-decene which is a relative volatility of 1.63.

Example 3

Sixty grams of 1-decene, 50 grams of decane and 150 grams of methyl t-butyl ether were placed in the stillpot of a 5.6 theoretical plate glass perforated plate rectification column and refluxed for four hours. The overhead composition was 14.4% decane, 85.6% 1-decene; the bottoms composition was 57.6% decane, 42.4% 1-decene which is a relative volatility of 1.45.

I claim:

1. A method for recovering decene-1 from a mixture of decene-1 and decane which comprises distilling a mixture of decene-1 and decane in the presence of an azeotrope forming agent, recovering the azeotrope forming agent and the decene-1 as overhead product and obtaining the decane from the stillpot, wherein said azeotrope forming agent consists of one material selected from the group consisting of methyl acetate, methyl formate, methyl propionate, ethyl butyrate, methyl t-butyl ether, t-amyl methyl ether and isopropyl ether.

* * * * *